(12) United States Patent
Vankipuram et al.

(10) Patent No.: US 12,023,176 B2
(45) Date of Patent: Jul. 2, 2024

(54) EXTENDED REALITY ADJUSTMENTS BASED ON PHYSIOLOGICAL MEASUREMENTS

(71) Applicant: Hewlett-Packard Development Company, L.P., Spring, TX (US)

(72) Inventors: Mithra Vankipuram, Palo Alto, CA (US); Rafael Ballagas, Palo Alto, CA (US); Kevin Smathers, Palo Alto, CA (US)

(73) Assignee: Hewlett-Packard Development Company, L.P., Spring, TX (US)

(*) Notice: Subject to any disclaimer, the term of this patent is extended or adjusted under 35 U.S.C. 154(b) by 316 days.

(21) Appl. No.: 17/414,356

(22) PCT Filed: Jun. 12, 2019

(86) PCT No.: PCT/US2019/036794
§ 371 (c)(1),
(2) Date: Jun. 16, 2021

(87) PCT Pub. No.: WO2020/251567
PCT Pub. Date: Dec. 17, 2020

(65) Prior Publication Data
US 2022/0096010 A1    Mar. 31, 2022

(51) Int. Cl.
*G08B 23/00* (2006.01)
*A61B 5/00* (2006.01)
(Continued)

(52) U.S. Cl.
CPC ........ *A61B 5/6806* (2013.01); *A61B 5/02438* (2013.01); *A61B 5/0533* (2013.01);
(Continued)

(58) Field of Classification Search
CPC ..... A61B 5/742; A61B 5/7455; A61B 5/6806; A61B 5/0533; A61B 5/02438;
(Continued)

(56) References Cited

U.S. PATENT DOCUMENTS 10,771,844 B2 * 9/2020 Marci .............. H04N 21/42201
10,860,103 B2 * 12/2020 Kacelenga .............. G06F 3/011
(Continued)

FOREIGN PATENT DOCUMENTS

| AU | 2016205850 A1 | 7/2017 |
| CN | 107438398 A | 12/2017 |

(Continued)

*Primary Examiner* — Anh V La
(74) *Attorney, Agent, or Firm* — Quarles & Brady LLP

(57) ABSTRACT

In example implementations, an apparatus is provided. The apparatus includes a physiological sensor, a memory, and a processor. The physiological sensor is to measure a physiological parameter. The memory is to store an extended reality application and a baseline level for the physiological parameter. The processor is in communication with the physiological sensor and the memory. The processor is to execute the extended reality application. In response to the physiological parameter exceeding the baseline level by a difference threshold, the processor is to adjust the extended reality application.

20 Claims, 4 Drawing Sheets

(51) Int. Cl.
*A61B 5/024* (2006.01)
*A61B 5/0533* (2021.01)
*A61B 5/389* (2021.01)
*G02B 27/01* (2006.01)

(52) U.S. Cl.
CPC .............. *A61B 5/389* (2021.01); *A61B 5/742* (2013.01); *A61B 5/7455* (2013.01); *G02B 27/017* (2013.01); *A61B 2560/0223* (2013.01)

(58) Field of Classification Search
CPC ............ A61B 5/389; A61B 2560/0223; A61B 5/0205; G02B 27/017; A63F 13/212; A63F 13/25; A63F 13/285; A63F 2300/8082; A63F 13/67
USPC ................ 340/573.1, 407.1, 407.2, 574, 575
See application file for complete search history.

(56) References Cited

U.S. PATENT DOCUMENTS

| | | | | |
|---|---|---|---|---|
| 10,877,444 | B1 * | 12/2020 | Roach | A61B 5/7405 |
| 11,229,385 | B2 * | 1/2022 | Baeuerle | A61B 5/7275 |
| 11,343,596 | B2 * | 5/2022 | Chappell, III | G16H 50/30 |
| 11,568,166 | B1 * | 1/2023 | Rainaldi | H04W 4/21 |
| 11,602,293 | B2 * | 3/2023 | Bach | A61B 5/16 |
| 2010/0217099 | A1 * | 8/2010 | LeBoeuf | A61B 5/6815 600/301 |
| 2013/0338490 | A1 | 12/2013 | Wendler | |
| 2014/0278220 | A1 | 9/2014 | Yuen | |
| 2014/0316191 | A1 | 10/2014 | de Zambotti et al. | |
| 2016/0054797 | A1 | 2/2016 | Tokubo et al. | |
| 2016/0077547 | A1 | 3/2016 | Aimone et al. | |
| 2018/0190376 | A1 * | 7/2018 | Hill | A61B 5/375 |
| 2019/0279768 | A1 * | 9/2019 | Bates | A61B 5/316 |
| 2020/0206631 | A1 * | 7/2020 | Sumant | A63F 13/55 |
| 2020/0405213 | A1 * | 12/2020 | Chappell, III | G16H 50/30 |
| 2023/0233123 | A1 * | 7/2023 | Rahman | A61B 5/02405 600/300 |

FOREIGN PATENT DOCUMENTS

| | | |
|---|---|---|
| CN | 107708548 A | 2/2018 |
| KR | 100956406 | 5/2010 |
| WO | WO-2006091822 A2 | 8/2006 |
| WO | WO-2017059215 | 4/2017 |
| WO | WO-2018063521 | 4/2018 |
| WO | WO-2018094232 | 5/2018 |
| WO | WO-2018218356 | 12/2018 |

* cited by examiner

EXTENDED REALITY ADJUSTMENTS BASED ON PHYSIOLOGICAL MEASUREMENTS

BACKGROUND

Virtual reality (VR) applications provide new experiences for users. The VR applications can provide an artificial environment created via software. The VR systems may include a range of hardware. For example, the VR systems may include an entire enclosure where the user can feel movement as the enclosure moves, or may include a head mounted display that can be worn by the user.

DETAILED DESCRIPTION

Examples described herein provide an XR system or HMD that can make XR adjustments based on physiological measurements. In one example, extended reality (XR) may be defined to include virtual reality (VR) devices and applications, augmented reality (AR) devices and applications, mixed reality (MR) devices, and applications, and the like.

As discussed above, VR applications provide new experiences for users. Some VR systems include a head mounted display that can be used with gloves that provide controls.

Some VR applications can provide a realistic experience to a user. The VR system can provide haptic feedback, as well as audio and video effects that can make the VR environment appear and feel real to the user. However, some VR experiences can be too realistic for the user and cause the user discomfort.

Some VR applications may benefit from the use of physiological or biometric data. The physiological data may help the VR application make adjustments in real-time. In addition, the physiological data may allow the VR application to personalize the VR experience for each user.

Examples herein provide an XR system or HMD that includes physiological sensors that can measure physiological parameters or biometric data. The sensors may be included in the gloves, the controllers, the HMD, and the like.

In some examples, a calibration application may be included in the XR application to collect physiological data to create a baseline level for various physiological parameters. The physiological parameters may include heart rate, galvanic skin response (GSR), electromyography (EMG) data, and the like. The physiological sensors can measure the physiological parameters of the user during the XR experience to determine if any of the physiological parameters of the user are exceeding the baseline level established during the calibration application.

When the baseline levels are exceeded, the XR system may adjust the XR application or experience. For example, the XR system may adjust a level of haptic feedback, adjust visual effects, adjust audio effects, and the like. As a result, the XR experience may be customized to a comfort level of a user that may be different than the comfort levels of other users.

Figure 1:
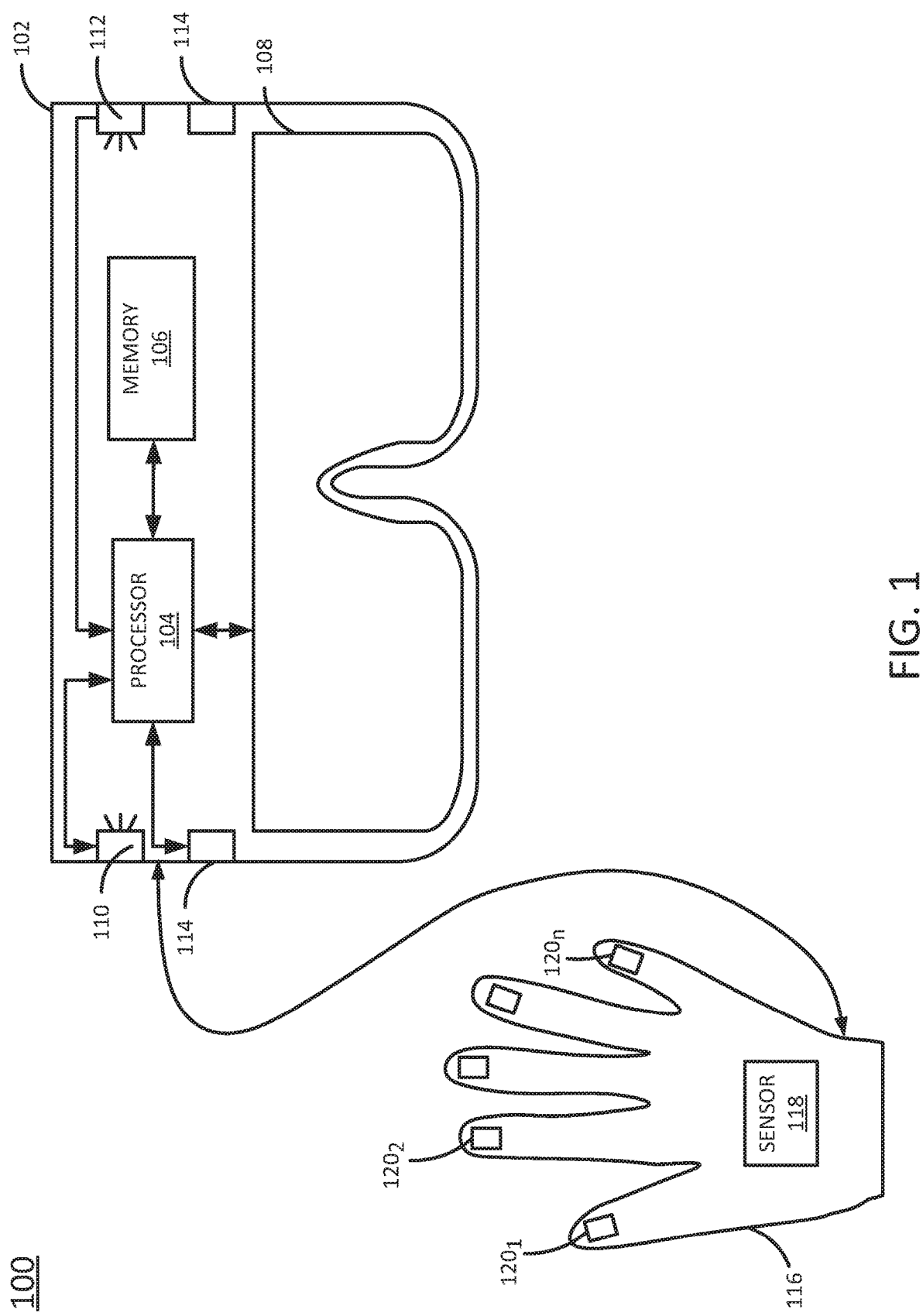
FIG. 1 is a block diagram of an example extended reality (XR) system with physiological sensors of the present disclosure.

FIG. 1 illustrates an example XR system 100 of the present disclosure. As noted above, XR may include VR, AR, or MR. In one example, the XR system 100 may include an XR head mounted display (HMD) 102 and a glove 116. Although a single glove 116 is illustrated in FIG. 1, it should be noted that two gloves 116 may be deployed. In one example, the XR system 100 may include a backpack or separate controller (not shown) that is communicatively coupled to the XR HMD 102 and the glove 116. The separate controller may offload processing from the XR HMD 102 to allow the XR HMD 102 to have a smaller footprint and design.

In one example, the XR HMD 102 may include a display 108 and speakers 110 and 112. The display 108 may be a pass-through display that allows for VR applications and augmented reality (AR) applications. The display 108 may show the XR environment or applications that are executed by the XR system 100. The speakers 110 and 112 may play audio associated with the XR environment or applications.

In one example, the XR HMD 102 may include a sensor 114 to measure a physiological parameter of a user. The sensor 114 may be a physiological sensor such as an electrode that can contact the skin of a user and collect physiological information. For example, the sensor 114 may monitor or measure physiological parameters such as a heart rate, a galvanic skin response (GSR), electromyography (EMG) data, and the like.

As discussed in further details below, the physiological parameters can provide information that indicates how a user is responding to the XR application. For example, the amount of visual information, audio information, haptic feedback, and the like may be determined to be too stimulating for a user based on the physiological parameters that are measured. In response, the XR application may be adjusted (e.g., the video effects, the audio effects, and/or the haptic feedback) for the user in accordance with the physiological parameters that are measured.

In one example, the XR HMD 102 may include a processor 104 and a memory 106. The processor 104 may be communicatively coupled to the memory 106, the display 108, the speakers 110 and 112, and the sensor 114. The processor 104 may receive the physiological parameters measured by the sensor 114 and control operation of the display 108, the speakers 110 and 112, and/or any haptic feedback devices in response to the physiological parameters that are measured.

In one example, the memory 106 may be a non-transitory computer readable medium, such as for example, random access memory (RAM), read only memory (ROM), a hard disk drive, a solid state drive, and the like. The memory 106 may store various instructions executed by the processor. The memory 106 may also store various data that may be used by the processor to determine how the display 108, the speakers 110 and 112, and the haptic feedback devices are to be controlled in response to the physiological parameters that are measured by the sensors 114.

In one example, the glove 116 may be communicatively coupled to the XR HMD 102 to provide controls to the XR application displayed by the XR HMD 102. Although illustrated as a glove 116 in FIG. 1, it should be noted that the glove 116 may be deployed as a different control device that can be held (e.g., a joystick, a glove like contraption, and the like).

In one example, the glove 116 may include a sensor 118. The sensor 118 may be a physiological sensor to collect and/or measure physiological parameters. The sensor 118 may also be an electrode or other type of monitoring device that can capture physiological parameters, such as, heart rate, GSR, EMG, and the like. In one example, the sensor 118 may be deployed in the glove and the sensors 114 may be removed from the XR HMD 102. In one example, the sensors 114 may be deployed without the sensor 118 in the glove 116.

In one example, both the sensors 114 and 118 may be deployed. For example, the sensors 114 and 118 may be different types of sensors that are optimally located in either the XR HMD 102 or the glove 116 to measure particular physiological parameters. For example, the sensors 114 may be EMG sensors and the sensor 118 may be a GSR sensor. A second glove 116 on the other hand of the user may include heart rate monitor sensor, and so forth. The physiological information that is measured and collected may be transmitted to the processor 104 for analysis.

In one example, the glove 116 may also include haptic feedback devices $120_1$-$120_n$ (hereinafter referred to individually as a haptic feedback device 120 or collectively as haptic feedback devices 120). Although multiple haptic feedback devices 120 are illustrated in FIG. 1, it should be noted that a single haptic feedback device 120 may also be deployed. In addition, although the haptic feedback devices 120 are illustrated as being in the fingertips of the glove 116, it should be noted that the haptic feedback devices 120 may be deployed anywhere in the glove 116. The haptic feedback devices 120 may also be deployed in the XR HMD 102.

In one example, the haptic feedback devices 120 may provide haptic feedback that is associated with events or actions viewed in the XR application. The haptic feedback devices 120 may provide haptic feedback such as stretching skin on the finger of a user, a vibration, a texture, a pulsing sensation, and the like. The haptic feedback can help the user feel as if they are holding an object, feel the texture of the object being held or touched in the XR application, and so forth.

In one example, other types of wearable devices can be deployed other than the HMD 102 and the glove 116. For example, the sensors 114 and 118 may also be deployed in wearable devices such as a watch, a vest, shoes, and the like, that can be communicatively coupled to the HMD 102.

As noted above, during execution of an XR application, the physiological parameters of a user may be measured. The processor 104 may adjust video effects, audio effects, or the haptic feedback that is experienced by a user based on the physiological parameters that are measured. The video effects, the audio effects, and the haptic feedback may be adjusted independently of one another or may be adjusted together as part of a multi-modal experience.

Figure 2:
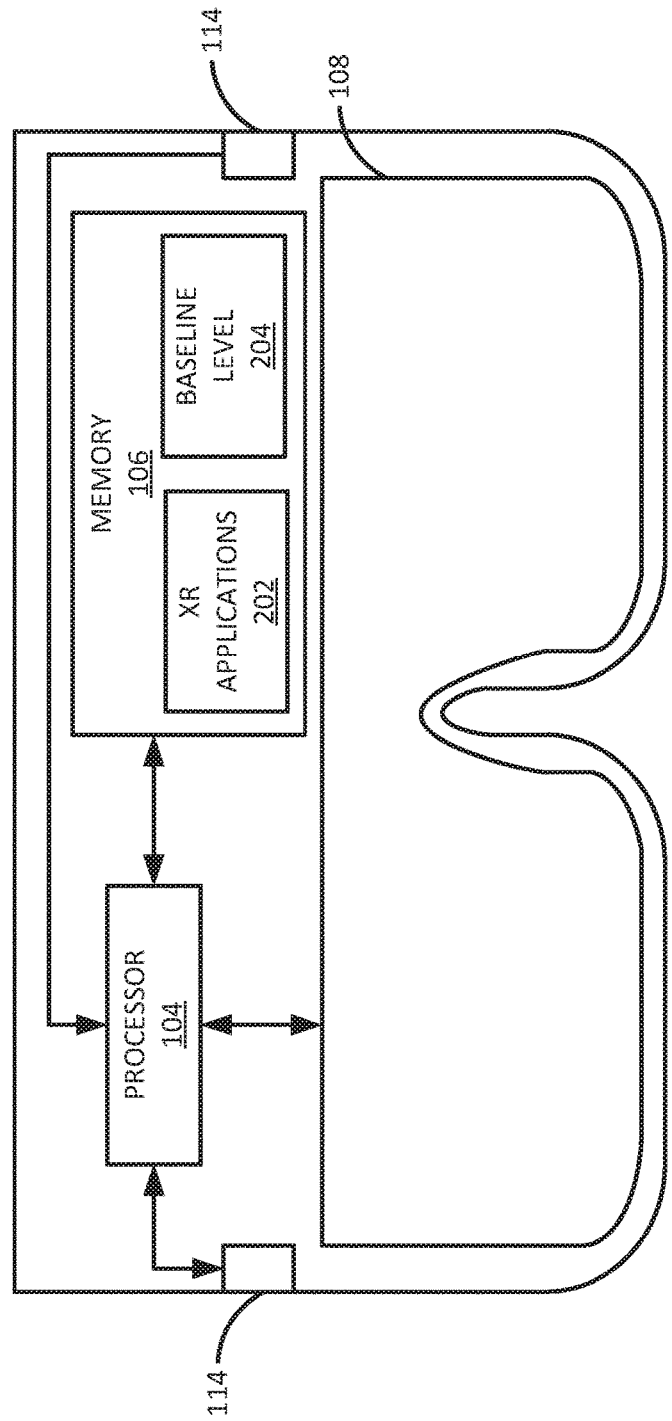
FIG. 2 is a block diagram of an example of a XR head mounted display (HMD) with physiological sensors of the present disclosure.

FIG. 2 illustrates another block diagram of the XR HMD 102. The XR HMD 102 may include the processor 104, the memory 106, the display 108, and the sensors 114, as illustrated in FIG. 1. In one example, the memory 106 may store a XR application 202 and a baseline level 204. The XR application 202 may include instructions executed by the processor to launch or run an XR application (e.g., an XR training experience, an XR game, and so forth).

In one example, the XR application 202 may also include a calibration application. The calibration application may be an initial portion of the XR application 202 or may be a completely separate application that can be stored in the memory 106 and executed by the processor 104.

In one example, the calibration application may expose the user to various different types of video effects, audio effects, and/or haptic feedback to measure the physiological parameters of the user in response to the known effects. The physiological parameters that are measured may be averaged to generate the baseline level 204.

In one example, the baseline level 204 may include an average response or measurement values for different physiological parameters. For example, a baseline level may be associated with a heart rate, a baseline level may be associated with a GSR, a baseline level may be associated with the EMG parameter, and so forth.

In one example, the calibration application may be used to categorize the user into a particular group based on the user's responses. The baseline level 204 associated with the group may then be assigned to the user. For example, the user may be a "high sensitivity group" based on the user's responses to the calibration application. The high sensitivity group may have a relatively low baseline level 204. A different user may be a "normal" group based on the user's responses to the calibration application. The normal group may have a baseline level 204 that is higher than the high sensitivity group and lower than a low sensitivity group.

In another example, the baseline level 204 may be obtained from external data. For example, the baseline level 204 may be an average of measured physiological parameters of a test group of people. Thus, the baseline level 204 may be either associated with a particular individual or may be a general average of a previous group of individuals who were tested.

In one example, the baseline level 204 may also include a difference threshold. The difference threshold may be associated with each one of the physiological parameters or may be a global difference threshold that applies to each one of the physiological parameters.

The difference threshold may be a value or percentage that indicates that the physiological parameter of the user is exceeding the baseline level 204 for the physiological parameter by too large of a value. When this occurs, the user may be feeling discomfort or may be too simulated by the video effects, the audio effects, and/or the haptic feedback provided by the XR application 202.

In one example, the difference threshold may be dynamically changed based on user responses. For example, the difference threshold may be different for different users of the same XR application. The difference threshold may be dynamically set for a particular user based on the responses received during the calibration application used to establish the baseline level 204. For example, the calibration application may gradually show increasing haptic feedback scenes and ask the user to indicate when he or she feels uncomfortable. The response from the user may be used to set the difference threshold for the user.

For example, the difference threshold may be 125% and the baseline level 204 for heart rate may be 90 bpm. Thus, when the heart rate that is measured exceeds 112.5 bpm, then the XR application may be adjusted. The user may be experiencing a battle scene in the XR application and the sensor 118 may measure the heart rate to be 120 bpm.

The processor 104 may determine that the 125% difference threshold has been exceeded for heart rate. In response, the processor 104 may adjust the XR application 202. For example, the processor 104 may reduce the haptic feedback generated by the haptic feedback devices 120 (e.g., reducing the amount of vibration when the user is shooting a rifle in the battle scene), may reduce the number of enemies seen in the battle scene, may lower the volume of the explosions or other sound effects in the battle scene, may adjust a brightness or dynamic range of the video, and so forth.

In one example, the difference threshold may also be to keep the physiological parameter above the baseline level 204. For example, an XR application may be an exercise application designed to keep the heart rate at an elevated level of 120 bpm. The difference threshold may be 20% above or below the baseline threshold. Thus, when the heart rate drops below 96 bpm, the processor 104 may determine that the user is bored or disengaged and increase the haptic feedback generated by the haptic feedback devices 120 (e.g., increasing the intensity of activities in the XR application, playing more upbeat music, and the like).

In one example, the physiological parameters may be continuously monitored or may be monitored in a rolling time window (e.g., every 60 seconds, every 5 minutes, every 10 minutes, and the like). When the physiological parameters fall back below the difference threshold, the XR application 202 may be returned to a default setting for the haptic feedback, video effects, and/or audio effects.

Figure 3:
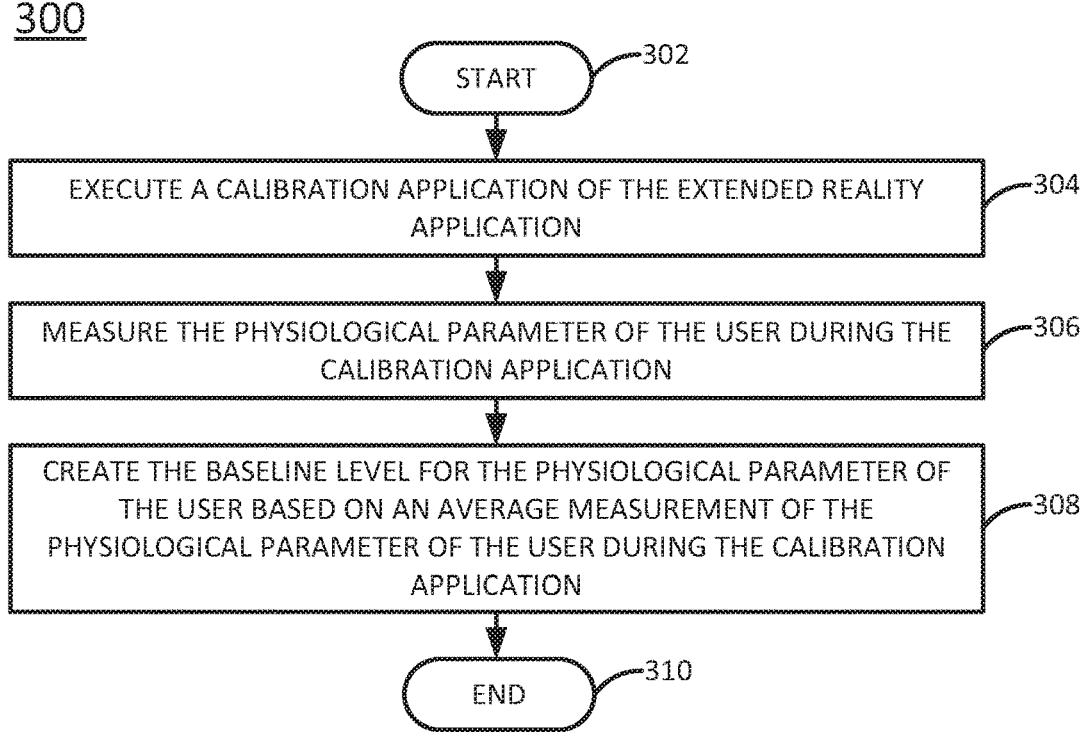
FIG. 3 illustrates a flow chart of an example method to create a baseline response level for a physiological parameter for a user of the present disclosure.

FIG. 3 illustrates a flow chart of an example method to create a baseline response level for a physiological parameter for a user of the present disclosure. In one example, the method 300 may be performed by the XR system 100 illustrated in FIG. 1 or the XR HMD 102 illustrated in FIGS. 1 and 2.

At block 302, the method 300 begins. At block 304, the method 300 executes a calibration application of the XR application. In one example, the calibration application may be executed initially before the XR application is executed. For example, each different XR application may have a unique calibration application that can establish the baseline response level for that particular XR application for the user. For example, some XR applications may provide more stimulation than other applications. For example, it may be normal for a user to have higher levels of GSR, EMG, and heart rate in a thrilling fighter jet simulator XR application than a training XR application for a job.

At block 306, the method 300 measures the physiological parameter of the user during the calibration application. The physiological parameters may be measured by sensors located in the XR HMD or the glove of the XR system. Different sensors may be used to measure different physiological parameters. For example, the physiological parameters may include heart rate, GSR, EMG, and the like.

At block 308, the method 300 may create the baseline level for the physiological parameter of the user based on an average measurement of the physiological parameter of the user during the calibration application. For example, the values of the physiological parameter may be periodically measured and divided by the total number of measurements to obtain the baseline response level for a physiological parameter. The baseline level may be for the user or may be for a group that the user is assigned to, as discussed above.

In one example, a difference threshold may be associated with the baseline level. As noted above, the difference threshold may be a value or percentage that indicates the physiological parameter is at a level that is unacceptable relative to the baseline level. The difference threshold may be different for different XR applications and for different physiological parameters. For example, the difference threshold may be larger for intense XR applications (e.g., battle games, skydiving simulations, horror games, and the like). The difference threshold may be smaller for less intense XR applications (e.g., training simulations, sightseeing simulations, observing 3D objects, and the like).

The baseline level and the difference threshold may be used by the XR system to adjust the XR applications when the physiological parameter of the user exceeds the difference threshold during the XR application. As noted above, the XR application can be adjusted by adjusting an amount of haptic feedback, video effects, audio effects, and the like. At block 310, the method 300 ends.

Figure 4:
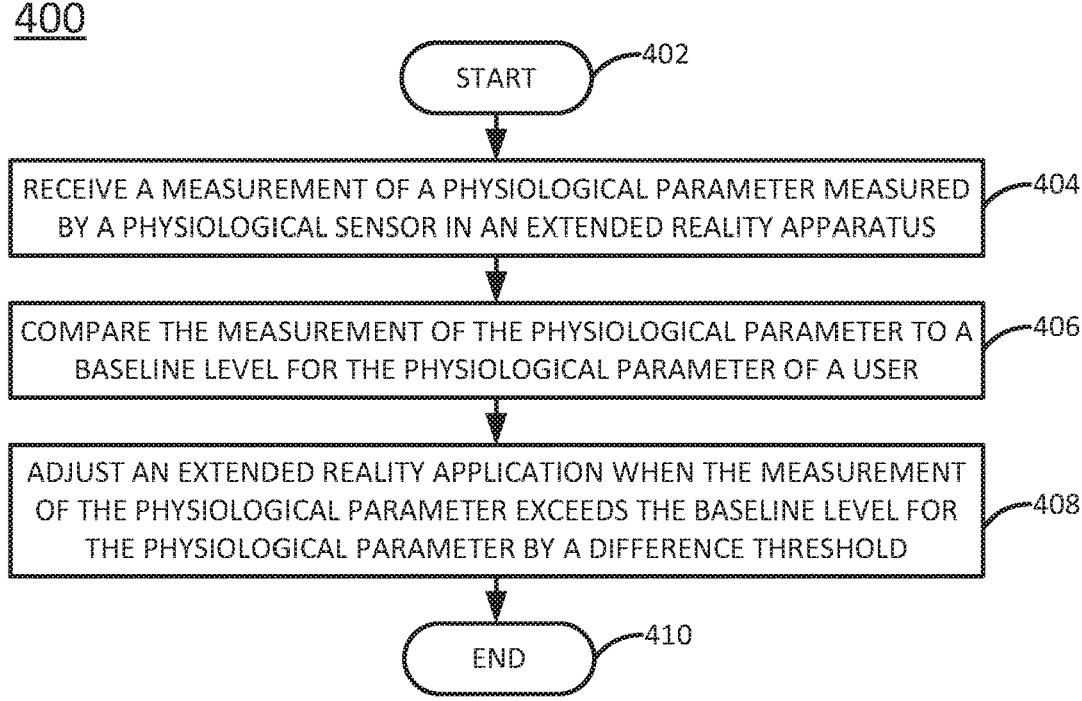
FIG. 4 illustrates a flow chart of an example method for adjusting an extended reality application based on a physiological measurement of the present disclosure.

FIG. 4 illustrates a flow chart of an example method for adjusting an extended reality application based on a physiological measurement of the present disclosure. In an example, the method 400 may be performed by the XR system 100 illustrated in FIG. 1 or the XR HMD 102 illustrated in FIGS. 1 and 2.

At block 402, the method 400 begins. At block 404, the method 400 receives a measurement of a physiological parameter measured by a physiological sensor in an extended reality apparatus of the processor. For example, the user may be wearing a XR HMD and a glove to provide control input to the XR application that is being executed by the XR HMD. The XR application may provide various different video effects, audio effects, and/or haptic feedback associated with the XR application.

The XR HMD and/or the glove may include physiological sensors that may measure the physiological parameters. The physiological parameters may include heart rate, GSR, EMG, and the like. The physiological parameters may vary as the user is consuming or experiencing the XR application.

At block 406, the method 400 compares the measurement of the physiological parameter to a baseline level for the physiological parameter of a user. In one example, each measurement may be compared to the baseline level. In one example, an average of a plurality of measurements captured in a rolling time period (e.g., every 5 seconds, every 60 seconds, every 5 minutes, and so forth) may be compared to the baseline level.

As discussed above, the baseline level may establish a particular value for the physiological parameter, or each one of a plurality of different physiological parameters, that is expected during the XR application. The baseline level may be also different for different portions of the XR application. For example, certain portions of the XR application may include more stimulation than other portions. Thus, the measurement of the physiological parameter may be compared to the baseline level for the physiological parameter and/or during an associated scene or portion of the XR application.

At block 408, the method 400 adjusts an extended reality application when the measurement of the physiological parameter exceeds the baseline level for the physiological parameter by a difference threshold. For example, if the physiological parameter that is measured exceeds the difference threshold, then the user may be uncomfortable or may be overly stimulated to an unsafe level. The different threshold may be wide enough to allow for some variations above the baseline level. However, the difference threshold may ensure that the user does not experience too much stimulation, or sustained stimulation at an unhealthy level.

In response to the difference level being exceeded, the method 400 may adjust the XR application. The adjustments may include adjustments to an amount of haptic feedback, content of the XR application, visual effects, and/or audio effects. In one example, the haptic feedback, the visual effects, and the audio effects may be modulated in isolation of one another (e.g., independently from one another). In one example, the haptic feedback, the visual effects, and the audio effects may be modulated together as part of a multi-modal experience.

In one example, the amount of haptic feedback provided by haptic feedback devices in the glove or the XR HMD may be reduced or eliminated. In one example, the adjustments to the visual effects may include making the graphics look less realistic, changing a brightness of the display, changing a dynamic range of the video, and the like. In one example, adjustments to content in the XR application may include reducing a number of enemies in a video game, shortening a particular scene in the XR application, and the like. In one example, the adjustments to the audio effects may include reducing a volume of the sound effects, eliminating certain sound effects, changing the frequency of some of the audio effects, and the like. Thus, the method 400 may automatically adjust the XR application to be a more comfortable and enjoyable experience for the user based on the measured physiological parameters of the user.

In one example, the method 400 may continuously measure the physiological parameters of the user throughout the XR application. Thus, if the physiological parameters return to a level that does not exceed the difference threshold, then the XR application may restore a default level of stimulation. In other words, the XR application may be continuously adjusted in response to the measured physiological parameters of the user throughout the entire XR application.

At block 410, the method 400 ends. For example, the XR application may be terminated to end the method 400.

Figure 5:
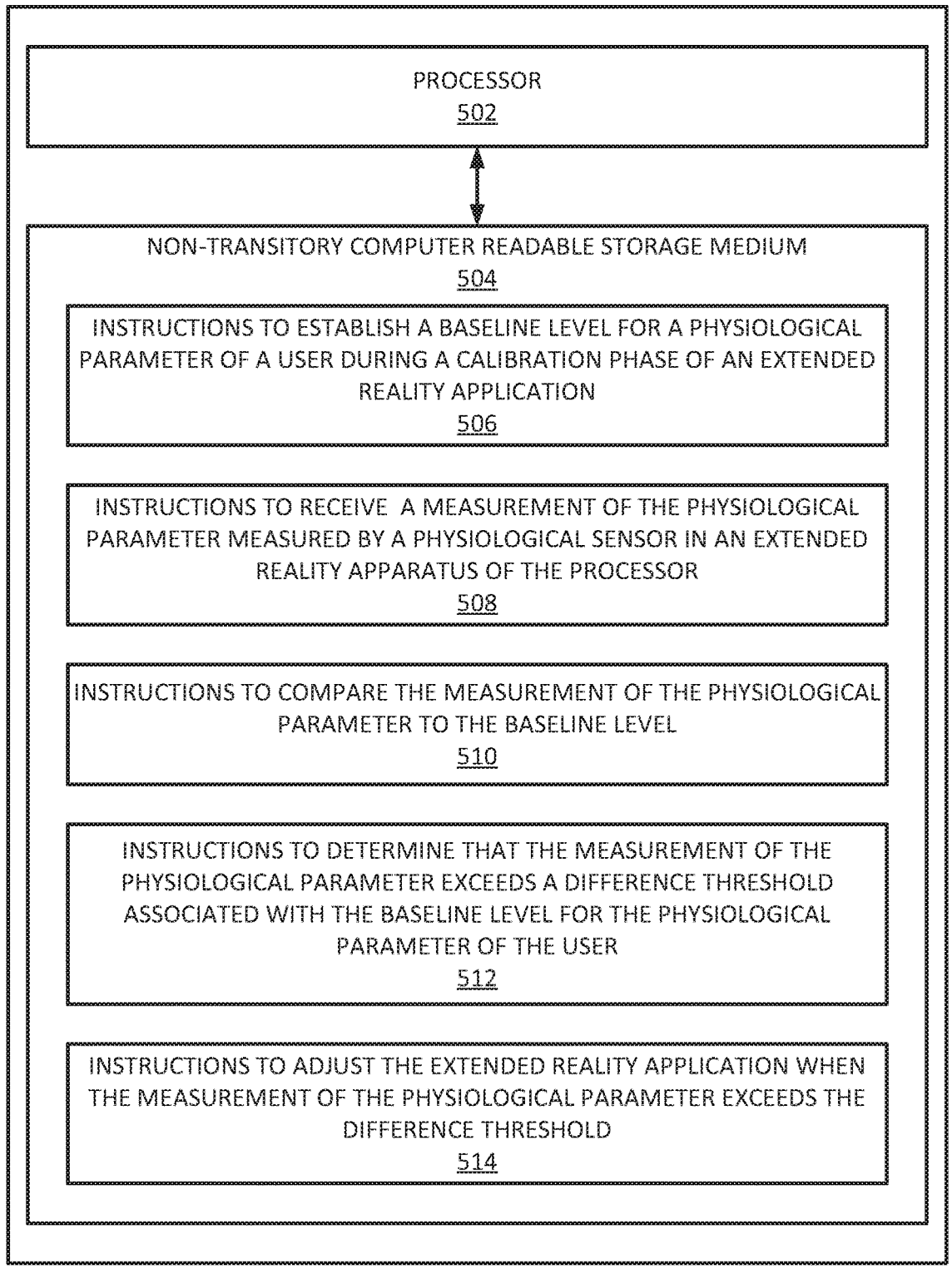
FIG. 5 is a block diagram of an example non-transitory computer readable storage medium storing instructions executed by a processor to adjust an extended reality application based on a physiological measurement of the present disclosure.

FIG. 5 illustrates an example of an apparatus 500. In one example, the apparatus 500 may be the apparatus 100. In one example, the apparatus 500 may include a processor 502 and a non-transitory computer readable storage medium 504. The non-transitory computer readable storage medium 504 may include instructions 506, 508, 510, 512, and 514, that, when executed by the processor 502, cause the processor 502 to perform various functions.

In one example, the instructions 506 may include instructions to establish a baseline level for a physiological parameter of a user during a calibration phase of an extended reality application. The instructions 508 may include instructions to receive a measurement of the physiological parameter measured by a physiological sensor in an extended reality apparatus of the processor. The instructions 510 may include instructions to compare the measurement of the physiological parameter to the baseline level. The instructions 512 may include instructions to determine that the measurement of the physiological parameter exceeds a difference threshold associated with the baseline level for the physiological parameter of the user. The instructions 514 may include instructions to adjust the extended reality application when the measurement of the physiological parameter exceeds the difference threshold.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. An apparatus, comprising:
   a physiological sensor to measure a physiological parameter associated with a user;
   a memory to store an extended reality application and a baseline level for the physiological parameter;
   a display to provide a video effect to the user in accordance with the extended reality application;
   a speaker to provide an audio effect to the user in accordance with the extended reality application; and
   a processor in communication with the physiological sensor, the display, the speaker, and the memory, the processor to:
     execute the extended reality application to provide the video effect and the audio effect to the user in accordance with the extended reality application;
     compare the measured physiological parameter associated with the user to the baseline level for the physiological parameter; and
     adjust at least one of the video effect or the audio effect provided to the user in accordance with the extended reality application responsive to determining that the measured physiological parameter associated with the user exceeds the baseline level for the physiological parameter by more than a difference threshold.

2. The apparatus of claim 1, wherein the apparatus comprises an extended reality head mounted display.

3. The apparatus of claim 1, wherein the physiological sensor is located in a glove controller in communication with the apparatus.

4. The apparatus of claim 1, further comprising:
   a haptic feedback device to provide haptic feedback to the user in accordance with the extended reality application;
   wherein the processor is to adjust the haptic feedback provided to the user in accordance with the extended reality application responsive to determining that the measured physiological parameter associated with the user exceeds the baseline level for the physiological parameter by more than the difference threshold.

5. The apparatus of claim 4, wherein the haptic feedback comprises stretching skin on the finger of the user, a vibration, a texture, or a pulse.

6. The apparatus of claim 1, wherein the processor is included in the display and the display comprises a head mounted display, the apparatus further comprising a backpack communicatively coupled to the head mounted display to offload processing from the head mounted display.

7. The apparatus of claim 1, wherein the physiological parameter comprises a heartrate, a galvanic skin response, or an electromyography.

8. The apparatus of claim 6, further comprising a glove communicatively coupled to the head mounted display and to the backpack, the glove comprising a haptic feedback device to provide haptic feedback to the user.

9. The apparatus of claim 8, wherein the processor is to adjust the haptic feedback provided to the user in accordance with the extended reality application responsive to determining that the measured physiological parameter associated with the user exceeds the baseline level for the physiological parameter by more than the difference threshold.

10. The apparatus of claim 9, wherein the physiological sensor is located in the glove.

11. A method, comprising:
    receiving, by a processor, a measurement of a physiological parameter associated with a user that is measured by a physiological sensor in an extended reality apparatus of the processor responsive to presentation of a video effect and an audio effect to the user via the extended reality apparatus in accordance with an extended reality application executed by the processor;

comparing, by the processor, the measurement of the physiological parameter associated with the user to a baseline level for the physiological parameter; and adjusting, by the processor, at least one of the video effect or the audio effect presented to the user via the extended reality apparatus in accordance with the extended reality application executed by the processor when the measurement of the physiological parameter exceeds the baseline level for the physiological parameter by more than a difference threshold.

12. The method of claim 11, further comprising:

executing, by the processor, a calibration application of the extended reality application;

measuring, by the processor, the physiological parameter associated with the user during execution of the calibration application; and creating, by the processor, the baseline level for the physiological parameter based on an average measurement of the physiological parameter associated with the user during execution of the calibration application.

13. The method of claim 12, comprising adjusting the difference threshold based on the average measurement of the physiological parameter associated with the user response during execution of the calibration application.

14. The method of claim 11, wherein comparing the measurement of the physiological parameter associated with the user to the baseline level for the physiological parameter comprises comparing the measurement of the physiological parameter associated with the user to the baseline level for the physiological parameter within a continuously rolling pre-defined time window.

15. The method of claim 11, wherein the adjusting comprises:

adjusting, by the processor, an amount of haptic feedback that is provided to the user in accordance with the extended reality application executed by the processor.

16. The method of claim 15, wherein adjusting, by the processor, the amount of haptic feedback that is provided to the user in accordance with the extended reality application executed by the processor comprises adjusting, by the processor, the amount of haptic feedback that is provided to the user via a haptic feedback device disposed in a glove that is communicatively coupled to the extended reality apparatus.

17. A non-transitory computer readable storage medium encoded with instructions executable by a processor, the non-transitory computer-readable storage medium comprising:

instructions to establish a baseline level for a physiological parameter associated with a user during execution of a calibration application of an extended reality application executed by the processor;

instructions to receive a measurement of the physiological parameter measured by a physiological sensor in an extended reality apparatus of the processor;

instructions to compare the measurement of the physiological parameter to the baseline level;

instructions to determine that the measurement of the physiological parameter exceeds a difference threshold associated with the baseline level for the physiological parameter associated with the user; and instructions to adjust at least one of a video effect or an audio effect presented to the user via the extended reality apparatus in accordance with the extended reality application executed by the processor when the measurement of the physiological parameter exceeds the difference threshold.

18. The non-transitory computer readable storage medium of claim 17, comprising instructions to receive a second measurement of a second physiological parameter associated with the user measured by the physiological sensor.

19. The non-transitory computer readable storage medium of claim 18, comprising instructions to adjust at least one of the video effect or the audio effect presented to the user via the extended reality apparatus in accordance with the extended reality application executed by the processor when the second measurement of the second physiological parameter that exceeds the difference threshold.

20. The non-transitory computer readable storage medium of claim 17, comprising instructions to adjust an amount of haptic feedback that is provided to the user via a haptic feedback device in accordance with the extended reality application executed by the processor when the measurement of the physiological parameter exceeds the difference threshold, the haptic feedback device disposed in a glove that is communicatively coupled to the extended reality apparatus.

* * * * *